(12) United States Patent
Vij

(10) Patent No.: US 8,320,990 B2
(45) Date of Patent: Nov. 27, 2012

(54) INTRABODY MRI STACKED FLAT LOOP ANTENNAS AND RELATED SYSTEMS

(75) Inventor: Kamal Vij, Chandler, AZ (US)

(73) Assignee: MRI Interventions, Inc., Memphis, TN (US)

(*) Notice: Subject to any disclaimer, the term of this patent is extended or adjusted under 35 U.S.C. 154(b) by 449 days.

(21) Appl. No.: 12/557,647

(22) Filed: Sep. 11, 2009

(65) Prior Publication Data
US 2010/0066371 A1     Mar. 18, 2010

Related U.S. Application Data

(60) Provisional application No. 61/096,525, filed on Sep. 12, 2008.

(51) Int. Cl.
*A61B 5/055* (2006.01)
(52) U.S. Cl. ........ 600/411; 600/374; 600/378; 600/423; 324/318; 324/322; 606/27; 606/41; 607/116; 607/122
(58) Field of Classification Search .......... 600/410, 600/411, 421–423, 373, 374, 378; 324/307, 324/309, 318, 322; 606/27, 41; 607/116, 607/119, 122
See application file for complete search history.

(56) References Cited

U.S. PATENT DOCUMENTS

| | | | |
|---|---|---|---|
| 4,947,854 A * | 8/1990 | Rabinovitz et al. | 600/453 |
| 5,078,736 A * | 1/1992 | Behl | 623/1.15 |
| 5,100,429 A * | 3/1992 | Sinofsky et al. | 623/1.21 |
| 6,050,992 A | 4/2000 | Nichols | |
| 6,167,311 A | 12/2000 | Rezai | |
| 6,284,971 B1 | 9/2001 | Atalar et al. | |
| 6,356,786 B1 | 3/2002 | Rezai et al. | |
| 6,405,079 B1 | 6/2002 | Ansarinia | |
| 6,438,423 B1 | 8/2002 | Rezai et al. | |
| 6,526,318 B1 | 2/2003 | Ansarinia | |
| 6,539,263 B1 | 3/2003 | Schiff et al. | |
| 6,609,030 B1 | 8/2003 | Rezai et al. | |
| 6,628,980 B2 * | 9/2003 | Atalar et al. | 600/423 |
| 6,708,064 B2 | 3/2004 | Rezai | |

(Continued)

FOREIGN PATENT DOCUMENTS
WO    WO 2007064739 A2 *   6/2007

OTHER PUBLICATIONS

International Search Report and Written Opinion for corresponding PCT Application No. PCT/US2009/005101, Date of mailing Apr. 6, 2010.
Hurst et al., Intravascular (Catheter) NMR Receiver Probe: Preliminary Design Analysis and Application to Canine Iliofemoral Imaging, Mag Res Med, 24: 343-357 (1992).
Martin et al., MR Imaging of Blood Vessels with an Intravascular Coil, SMRI, 421-429 (1992).

*Primary Examiner* — Ruth S Smith
(74) *Attorney, Agent, or Firm* — Myers Bigel Sibley & Sajovec, P.A.

(57) ABSTRACT

Elongate intrabody MRI-antenna probes include opposing distal and proximal portions. The distal portion includes at least one multi-turn conductor arranged as a stack of substantially flat loops, each with a substantially rectangular elongate shape. A flat loop can reside on each of a plurality of adjacent vertically stacked substantially planar layers, the flat loops cooperate to define a MRI receive antenna.

20 Claims, 12 Drawing Sheets

U.S. PATENT DOCUMENTS

| | | |
|---|---|---|
| 6,771,070 B2 | 8/2004 | Lee |
| 7,561,906 B2 | 7/2009 | Atalar |
| 2003/0050557 A1 | 3/2003 | Susil |
| 2007/0010895 A1* | 1/2007 | Gray et al. .................. 623/23.7 |
| 2008/0039709 A1 | 2/2008 | Karmarkar |
| 2008/0097193 A1 | 4/2008 | Karmarkar |
| 2008/0243218 A1 | 10/2008 | Bottomley |
| 2008/0306375 A1 | 12/2008 | Sayler |
| 2009/0112084 A1 | 4/2009 | Piferi |
| 2009/0171421 A1 | 7/2009 | Atalar |

\* cited by examiner

FLAT DOUBLE LOOP

CORONAL

AXIAL

EXPERIMENT PROTOCOL:

| Parameter: | Notes: |
|---|---|
| Phantom | Rectangular Nalgene bottle filled with saline solution inclined at 20 degree angle |
| Pulse Sequence | Spin Echo with 90° flip angle |
| Timing | TR = 500msec TE = 21msec |
| Slice | 5mm thick Axials and Coronals |
| Field Of View | 107mm * 107mm |
| Sampling | 512 * 512 points |
| Receiver Bandwidth | 160 KHz |
| Signal Averages | 1 |

FIG. 5

INTRABODY MRI STACKED FLAT LOOP ANTENNAS AND RELATED SYSTEMS

RELATED APPLICATIONS

This application claims priority to and the benefit of priority of U.S. Provisional Application Ser. No. 61/096,525, filed Sep. 12, 2008, the contents of which are hereby incorporated by reference as if recited in full herein.

FIELD OF THE INVENTION

The present invention relates to medical probes and may be particularly suitable for use in MRI interventional or diagnostic procedures.

SUMMARY OF EMBODIMENTS OF THE INVENTION

Embodiments of the present invention provide MRI imaging systems with probes that may be particularly suitable for intrabody imaging, such as imaging used during intracardiac, or deep brain diagnostic and/or interventional procedures.

Embodiments of the invention are directed to elongate intrabody MRI-antenna probes having opposing distal and proximal portions. The distal portion includes at least one conductor arranged in a stack of closely spaced substantially flat loops. The flat stacked loops cooperate to define an MRI signal receive antenna.

These devices can obtain MRI signals to render MRI images of the local anatomy and may be used to detect and/or measure the electrical pulses of the cardiac, cranial or other target tissue.

The systems may be used to guide or view various parts of the body, such as the brain and/or heart during a diagnostic or interventional procedure in substantially real-time MRI.

Some embodiments are directed to elongate intrabody MRI-antenna probes having opposing distal and proximal portions. The distal portion including at least one multi-turn conductor arranged as a substantially flat loop with a substantially rectangular elongate shape on each of a plurality of adjacent vertically stacked substantially planar layers. The stacked flat loops cooperating to define a receive antenna.

In some embodiments, each layer of the flat loop is defined by a conductor formed as the substantially rectangular elongate shape held by a flexible substrate, such that the flexible substrates are stacked one over the other to define the vertically stacked planar layers.

In particular embodiments, at least two of the flat loops are closed loops with one of the other layers having a conductor in communication with at least one capacitor, wherein the flat loop layers have an associated inductance, and wherein the probe is tuned to an operating frequency of an MRI scanner using the at least one capacitor and inductance of the flat loop layers of the probe.

In some embodiments, the flat loops have a long side and a short side, the long side having a length that is between about 20-50 mm, the short side having a width that is between about 1-5 mm.

The probe can also include: (a) an RF transmit decoupling circuit in communication with the conductor, the decoupler circuit configured to decouple the MRI antenna during an MRI RF excitation transmission; and may optionally include (b) a splitter circuit in communication with a recording, ablating and/or stimulation electrode to electrically isolate a recording circuit from an MRI imaging circuit and/or filters for allowing detection of local signal (e.g., EKG or electrophysiology signal).

Other embodiments are directed to MRI cardiac systems that include an intracardiac probe with at least one conductor configured in a stack of abutting layers of substantially flat loops. The stacked flat loops have a long side and a short side, the respective long sides having a length that is between about 20-50 mm and the respective short sides having a width that is between about 1-5 mm. The stacked flat loops cooperate to define an MRI signal receive antenna. The probe also includes or is in communication with matching and decoupling circuitry in communication with the receive antenna and an MRI scanner.

Yet other embodiments are directed to MRI neurological systems that include an intrabrain probe with at least one conductor configured in a stack of abutting layers of substantially flat loops. The stacked flat loops have a long side and a short side, the respective long sides having a length that is between about 20-50 mm and the respective short sides having a width that is between about 1-5 mm. The stacked flat loops cooperate to define an MRI signal receive antenna. The probe also includes or is in communication with matching and decoupling circuitry in communication with the receive antenna and an MRI scanner.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 5 is a table of experimental protocol used to evaluate a prototype imaging probe according to embodiments of the present invention.

DETAILED DESCRIPTION OF EMBODIMENTS OF THE INVENTION

Figure 1A:
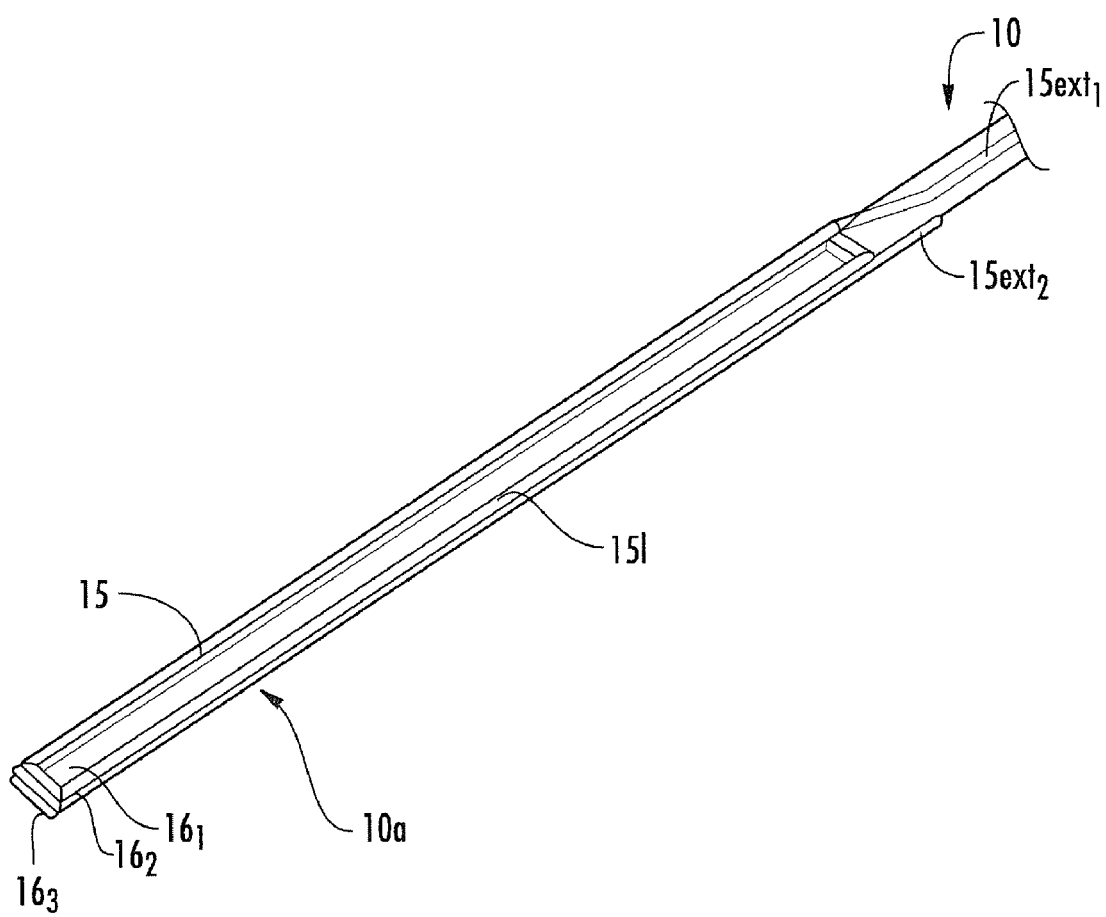
FIG. 1A is a top perspective view of an MRI antenna probe according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain antenna embodiment, features or operation of one probe or system embodiment can apply to others.

In the drawings, the thickness of lines, layers, features, components and/or regions may be exaggerated for clarity and broken lines illustrate optional features or operations, unless specified otherwise. In addition, the sequence of operations (or steps) is not limited to the order presented in the claims unless specifically indicated otherwise. It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms "first" and "second" are used herein to describe various components, regions, layers and/or sections, these regions, layers and/or sections should not be limited by these terms. These terms are only used to distinguish one component, region, layer or section from another component, region, layer or section. Thus, a first component, region, layer or section discussed below could be termed a second component, region, layer or section, and vice versa, without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the application and should not be interpreted in an idealized or overly formal sense unless expressly so defined herein.

Probe embodiments of the present invention can be configured to obtain signal data for an MR image, record or detect signal from local tissue and/or stimulate any desired internal region of the body or object. The object can be any object. Embodiments of the invention may be particularly suitable for animal and/or human subjects. Some probe embodiments can be sized and configured for deep brain procedures. Some probe embodiments can be configured to place stimulation electrodes to stimulate a desired region of the brain and/or sympathetic nerve chain. Other embodiments are directed to MRI-guided cardiac procedures, such as AFIB (atrial fibrillation) treatments. In some embodiments, the imaging probe can be introduced intravenously into the heart and guided to help identify locations for atrial wall punctures and/or to obtain signal data to generate high resolution images of lesions associated with ablation treatments. Examples of known treatments and/or target body regions are described in U.S. Pat. Nos. 6,708,064; 6,438,423; 6,356,786; 6,526,318; 6,405,079; 6,167,311; 6539,263; 6,609,030, and 6,050,992, the contents of which are hereby incorporated by reference as if recited in full herein.

The term "loop" refers to a fully closed or nearly closed shape or line associated with an MRI-compatible (non-ferromagnetic) conductor. The term "conductor" and derivatives thereof refer to a conductive trace, filar, wire, lead, (small-diameter) cable, flex circuit or other electrically conductive member. A single conductor may also be configured as a closely spaced bundle of filars or wires. The conductor can be in the form of a single continuous length. The conductor can be formed with one or more discrete filars, wires, cables, flex circuits, bifilars, quadrafilars or other filar or trace configuration, or by plating, etching, deposition, or other fabrication methods for forming conductive electrical paths. The conductor can be insulated. The conductor can also comprise any suitable MRI-compatible (and biocompatible) material such as, for example, MP35N drawn filled tubing with a silver core and an ETFE insulation on the drawn tubing, Nitinol, gold, copper, silver, platinum, iridium, MP35N, tantalum, titanium, L605, gold-platinum-iridium, gold-copper-iridium, gold-platinum, and the like.

The term "high-resolution" refers to images that have increased resolution (better SNR) relative to conventional images or images obtained with surface coils alone (e.g., typically at least about 4×, better SNR than images generated using the MRI Scanner without data from the intrabody-antenna 10a, provided by the probe).

Embodiments of the present invention may be particularly suitable for use with high-magnetic field MR Scanner systems. The term "high-magnetic field" refers to field strengths above about 0.5T, typically above 1.0T, and more typically between about 1.5T and 10T. In some embodiments, the field strength can be about 3.0T. MRI Scanners include closed bore and open bore systems. MRI scanners are well known to those of skill in the art and include, for example, the SIGNA 1.5T/3.0T from GE Healthcare: the ACHEIVA 1.5T/3.0T and the INTEGRA 1.5T from Philips Medical System; and the MAGNETOM Avanto, the MAGNETOM Espree, the MAGNETOM Symphony, and the MAGNETOM Trio, from Siemens Medical.

The terms "MRI Scanner and MR Scanner" are used interchangeably to refer to a Magnetic Resonance Imaging system and includes the magnet, the operating components, e.g., RF amplifier, gradient amplifiers and processors that direct the pulse sequences and that may directly or indirectly identify the scan planes.

FIG. 1A is a top perspective view of an MRI antenna probe 10 according to embodiments of the present invention. As shown, the probe 10 includes a substantially flat (multi-turn) loop of at least one conductor 15. The probe 10 can include a plurality of stacked substantially flat loops 15I that can be provided as vertically stacked layers of substantially aligned loops that cooperate to form an MRI signal receive antenna 10a. The probe 10 can be configured as a semi-flexible probe that can be guidably inserted into a target intrabody location. In some embodiments, the probe 10 can be guided into position in the body with a (peel-away) sheath covering the distal end portion of the probe. In some embodiments, the probe 10 can be guidably inserted into the body in a flexible catheter or sheath (such as those used in transseptal puncture kits). The stacked conductor(s) 15 can be encased in a suitable biocompatible flexible polymeric material (such as a molded overlayer to define a flat body on the distal end without raised surfaces). The distal end of the probe 10 may also be tapered for ease of insertion or may have a blunt end as shown. The loop 15I may be substantially in the form of a rectangle as shown or may be substantially oval.

The antenna 10a, can be configured to detect/receive MRI signals from a distance that is projected forward from the tip of the probe body by between about 1-2 min. The stacked loops 15I can also be described as a coil, e.g., receive coil. As shown, there can be a plurality, typically at least two, shown as three, stacked loops or layers $16_1$, $16_2$, $16_3$, of one conductor 15 that can form two or three loops 15I, e.g., a flat double loop or a flat triple loop stacked antenna. Although not shown, a plurality of conductors can be used to form the stacked loops one above another directly or interleaved with other conductors or layers/materials. In addition, although shown as three stacked loops, other numbers of loops 15I of one or more conductor(s) may be used, such as for example, up to about 30, typically between 3-10, such as, for example, about four, five, six, seven, eight, and nine.

One layer or loop of the conductor 15 can have a different configuration than the others, e.g., one can have a completely closed configuration such that one layer crosses over one side or end of one loop and merges into the next upper or lower layer and another can have an elongate multi-turn configuration with an open end portion so that, for example, an upper or lower long side of the third layer is open and extends away from the loops 15I toward a proximal end of the device. In other embodiments, the antenna 10a, can have a plurality of closely stacked loops 15I with one layer, e.g., $16_1$, having a leg extension 15ext that extends to the proximal portion of the probe and defines an electrical transmission path to upstream circuitry (e.g., matching/tuning circuit, decoupling circuit, and the like). A second layer, e.g., $16_3$, may have a leg extension 15ext, shown as $15ext_1$, and $15ext_2$, respectively, that can also extend to the proximal portion of the probe (side-by-side or under or over the first leg extension) and electrically connects to the upstream circuitry. One extension $15ext_1$, can (physically and/or electrically) connect to one circuit, e.g., the decoupling circuit and/or to the other extension $15ext_2$. In other embodiments only one of the layers or loops has the leg extension. The layers $16_1$, $16_2$, $16_3$, can be electrically insulated from each other.

Figure 1B:
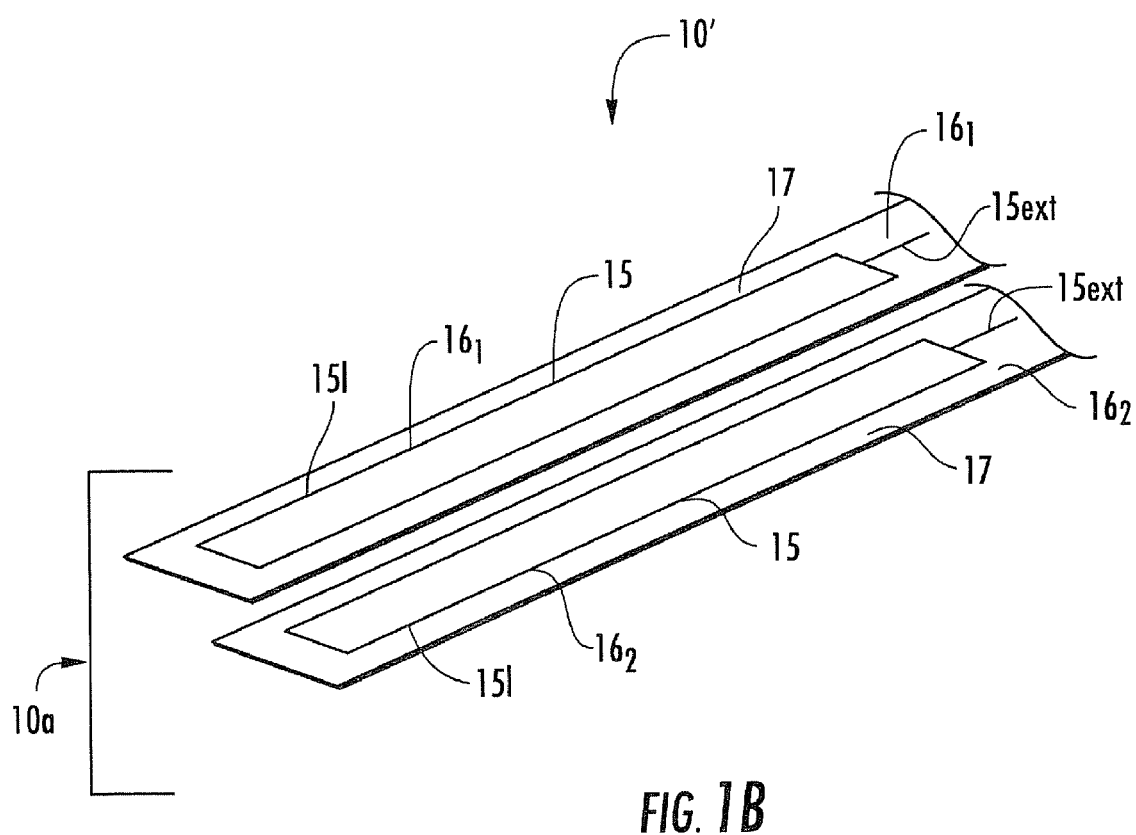
FIG. 1B is a partial exploded view of another MRI antenna probe according to embodiments of the present invention.

In other embodiments, as shown in FIG. 1B, at least two adjacent layers of stacked flex circuit substrates 17 (e.g., flex circuit boards) with the conductive loop 15I thereon or therein can be used to form the flat loop antenna 10a, of the imaging probe 10'. Greater numbers of layers and/or flat loops can be used. The flex substrates 17 can each include the flat conductive shape 15I or neighboring flat loops 15I can be separated by one or more flexible substrate layers with vias and/or other electrical paths used to connect the different substrates/loops as desired. To facilitate less intrusive procedures, it can be desirable to make the probe 10, 10' small, such as under 9 French, typically between about 2-8, French, and more typically between about 2-5, French. The probe may be configured for intrabody procedures, including, for example, intravenous, intralumen, intracavity or subcutaneous, e.g., deep brain procedures.

Figure 1C:
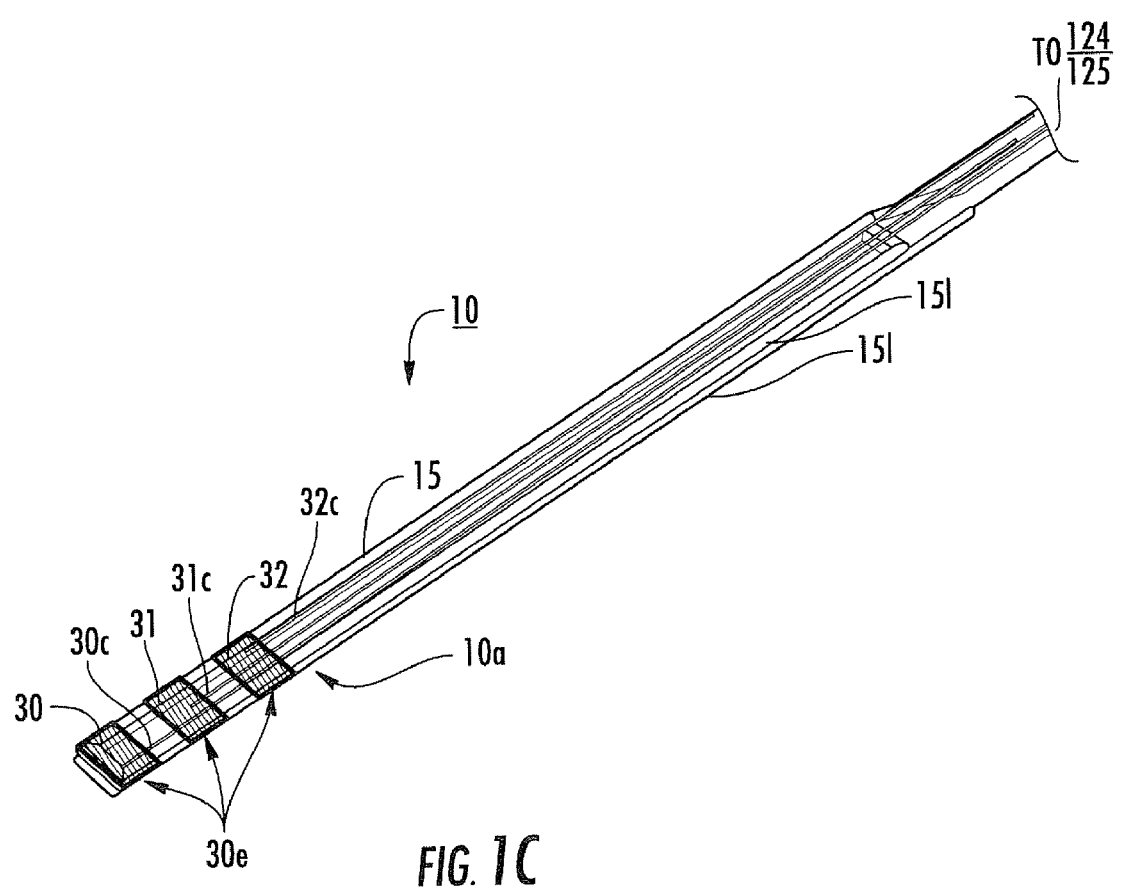
FIG. 1C is a top perspective view of a multi-purpose MRI antenna probe according to embodiments of the present invention.

As shown in FIGS. 1A-1C, the probe 10 can have flat loops 15I with a long side and a short side, the long side having a length that is between about 20-50 mm, the short side having a width that is between about 1-5 mm. In some embodiments, the long side is between about 30-40 mm, such as about 35 mm, and the short side is between 1-2 mm, such as about 1.5 mm. In some embodiments, the length of the loop 15I is between about 5-30 mm, typically between about 10-25 mm.

FIG. 1C also illustrates that the probe 10 can include at least one electrode 30e, shown as three axially spaced apart electrodes 30, 31, and 32. The electrodes and respective conductors can be electrically insulated from each other and the antenna conductor 15I. Each distal electrode 30, 31, 32, respectively, can include at least one conductor 30c, 31, 32c, (shown as a single conductor each) that is in electrical communication a proximal component, such as a biopotential amplifier or other output or input device. As is known to those of skill in the art, one electrode can be a reference electrode and another can be a recording electrode for sensing local electrical signal (e.g., potential, voltage and the like). One or more of the electrodes can couple with an external (pad) type electrode (typically attached to a back of a patient) as is well known to those of skill in the art. Thus, for example, two conductors 31c, 32c, can connect to a biopotential amplifier (the reference and the measuring electrode). In some embodiments, the probe electrodes can be sized and configured to detect and/or measure cardiac potential and in other embodiments the probe electrodes are sized and configured to measure and/or detect neural activity (e.g., during deep brain procedures). The tip electrode 30 can be an ablation or stimulation electrode. As will be discussed further below, the electrodes 30, 31, 32 can be in communication with a decoupling circuit. The probe 10 may include only ablation or stimulation electrodes or only recording electrodes and is not required to have both types of electrodes. The sensing electrode may also be used as the ablation or stimulation electrode.

Figure 2:
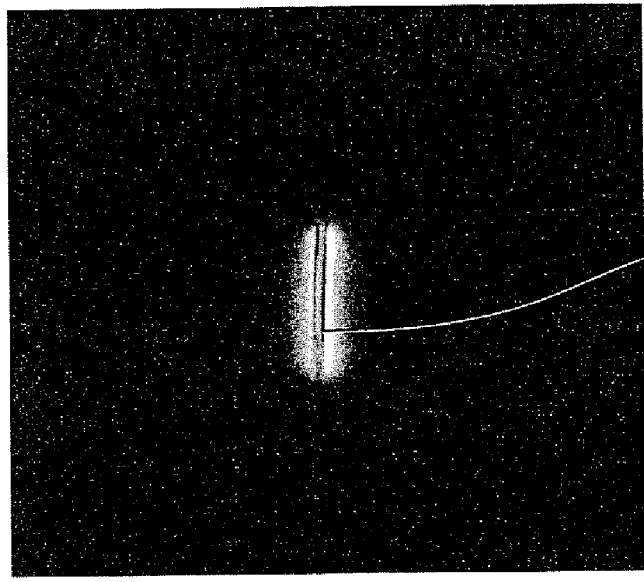
FIG. 2 are MRI images of the MRI antenna probe shown in FIG. 1A inside a sheath (coronal slice, top image, axial slice, bottom image) according to embodiments of the present invention.
Figure 2:
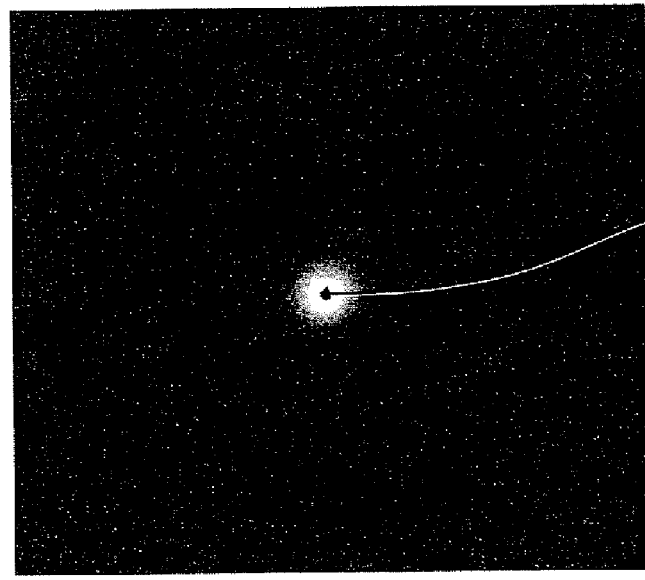

FIG. 2 illustrates MRI images of the MRI antenna probe shown in FIG. 1 inside a sheath 20 (FIG. 3) which may, in some embodiments, be a peel-away sheath. In FIG. 2, the top image is a coronal slice image and the bottom image is an axial slice image. The sheath 20 can be configured for intrabody use that can be left in place for guiding another interventional device after removing the antenna probe. The sheath 20 can be removed leaving the antenna and/or another interventional member in position as desired. In any event, as shown, the antenna 10a, is able to detect local MRI signal and generate a relatively strong signal (improved SNR) with at least about a 6 mm diameter signal penetration spot in an image.

Figure 3:
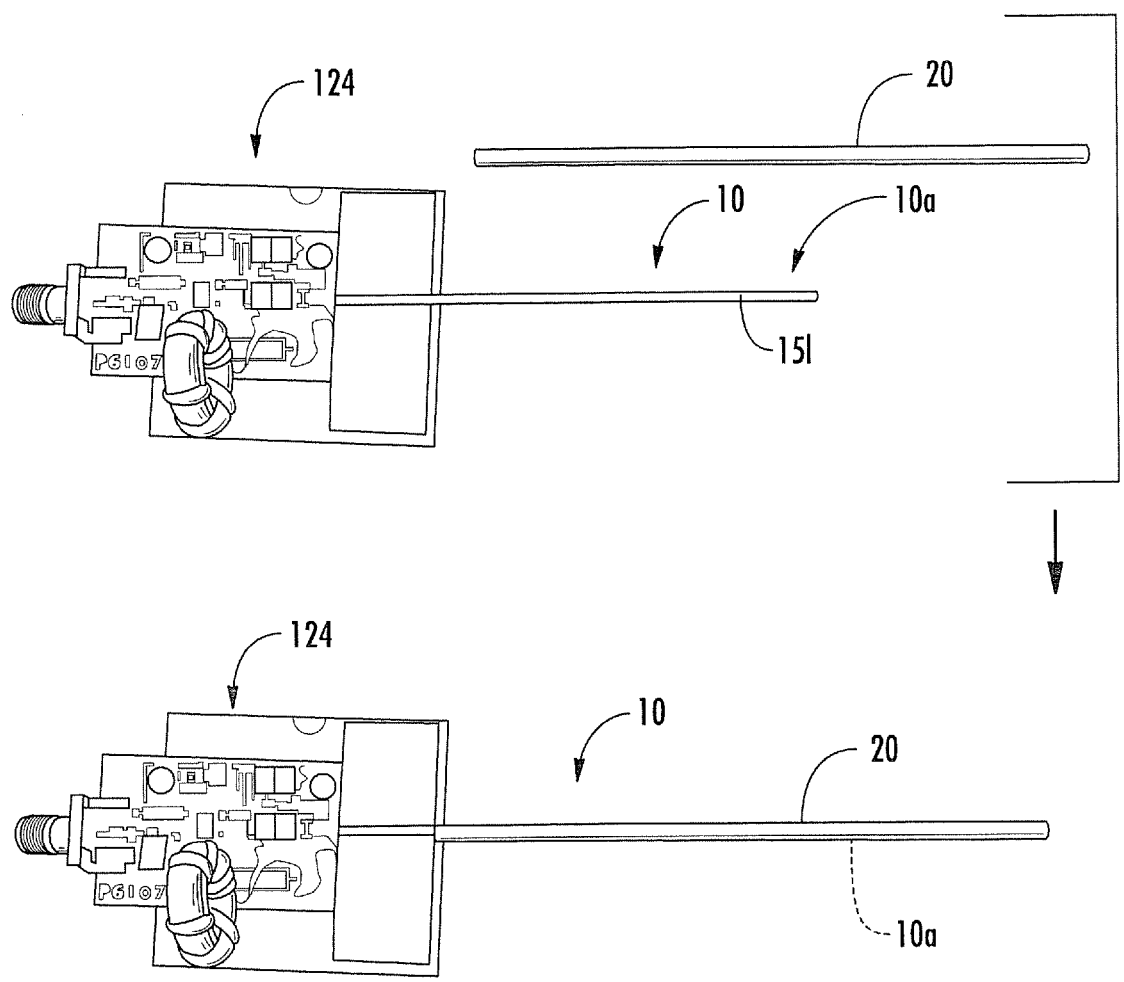
FIG. 3 are images of a prototype of the imaging probe with a sheath (the top shows the probe and sheath unassembled, the bottom shows the sheath on the probe) evaluated as shown in FIGS. 4 and 5 according to embodiments of the present invention.

FIG. 3 are images of a prototype of the imaging probe with a sheath (the top shows the sheath separate from the probe and the bottom shows the probe and sheath assembled) according to embodiments of the present invention. FIG. 3 illustrates the interface (matching/decoupling) circuit as a prototype build. It is contemplated that such circuitry will be miniaturized and integrated with the probe or a connector associated therewith.

Figure 4:
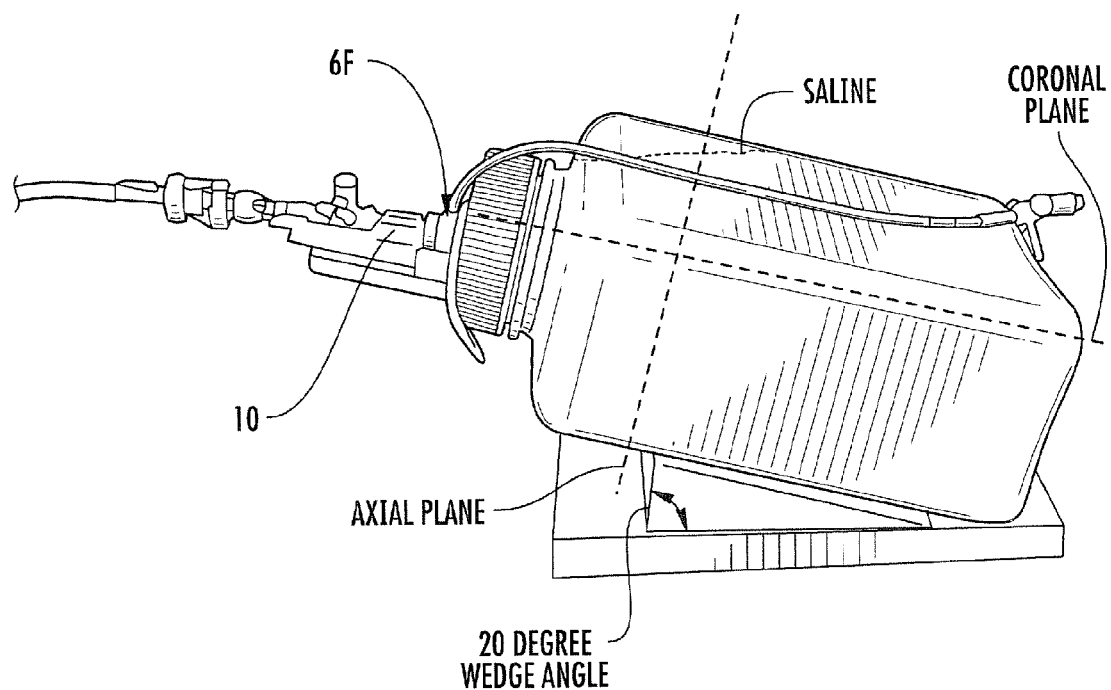
FIG. 4 is an illustration of an experimental set-up to obtain the images of FIG. 2 according to embodiments of the present invention.

FIG. 4 is an image of an experimental set-up to obtain the images of FIG. 2 according to embodiments of the present invention. FIG. 5 is a table of experimental protocol used to evaluate a prototype of the probe according to embodiments of the present invention.

Figure 6:
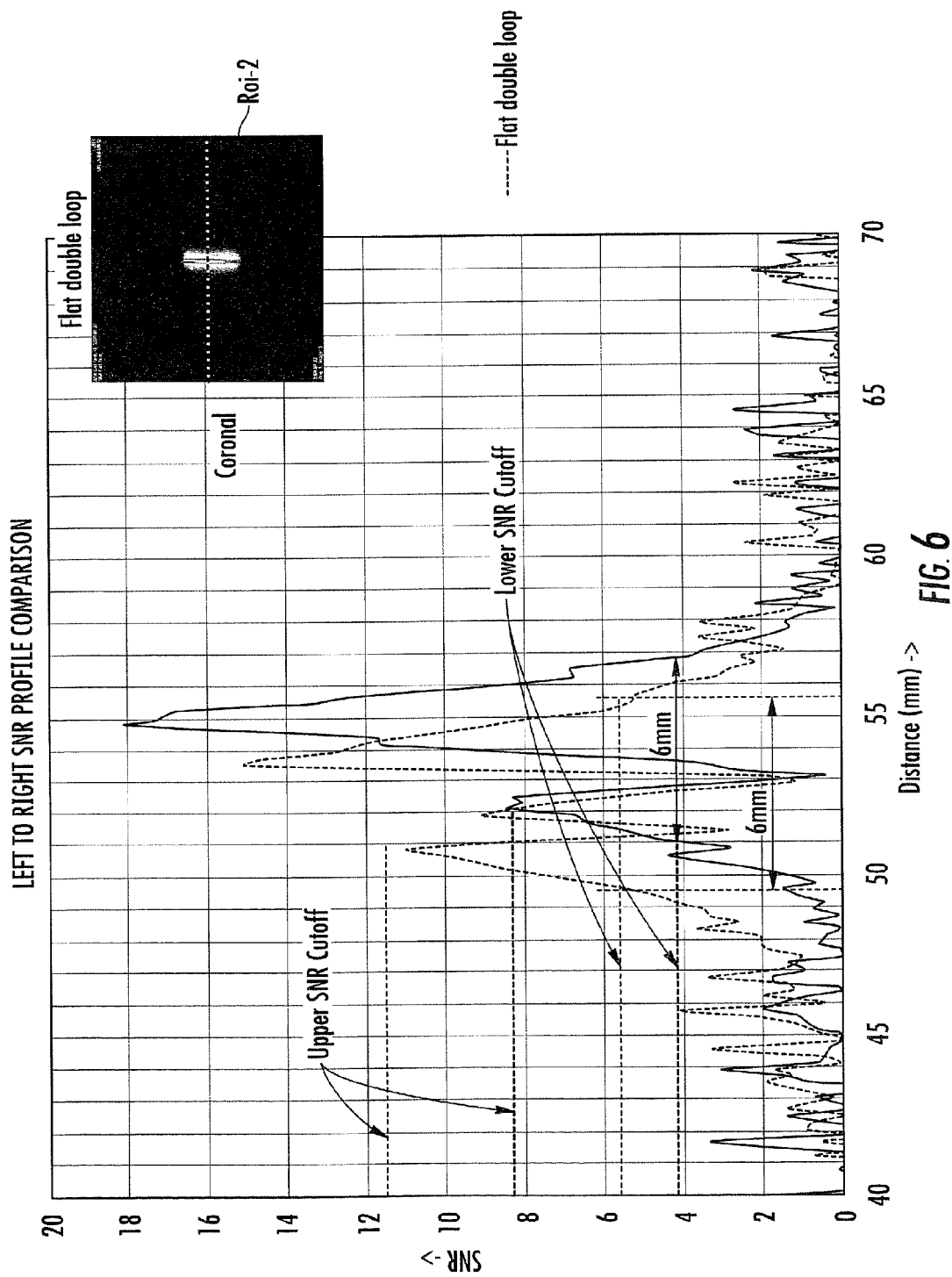
FIG. 6 is a graph of left to right SNR profile (SNR versus distance) of the antenna shown in FIG. 1 (the lighter shade data).
Figure 7:
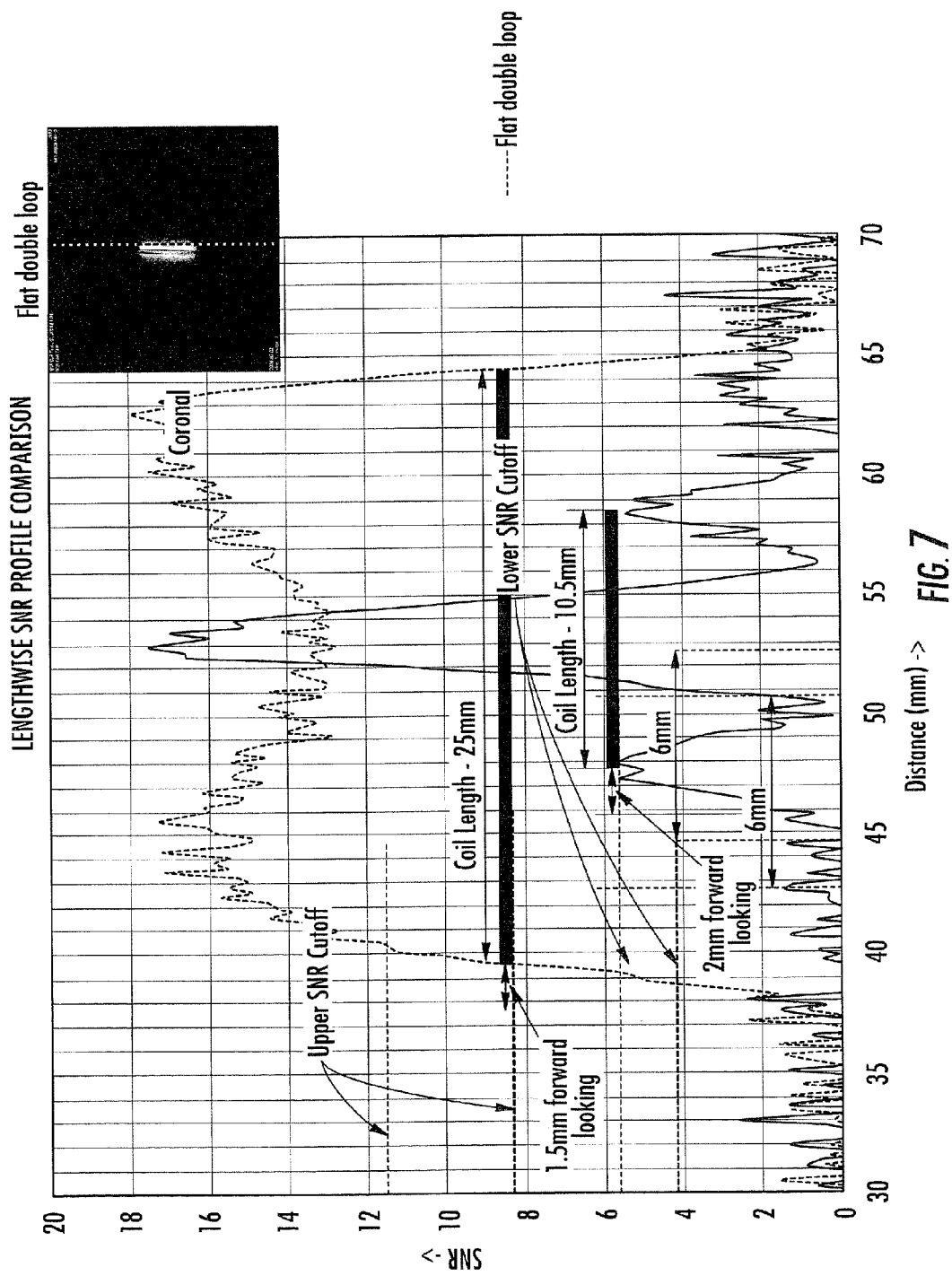
FIG. 7 is a graph of lengthwise SNR profile (SNR versus distance) of the antenna shown in FIG. 1 (the lighter shade data).

FIG. 6 is a graph of left to right SNR profile (SNR versus distance) of the imaging probe shown in FIG. 1 (broken line data) and FIG. 7 is a graph of lengthwise SNR profile (SNR versus distance) of the antenna 10a, shown in FIG. 1A (the broken line data). As shown, along the length, the flat loop antenna 10 produces a fairly homogenous signal profile and a forward looking distance of about 1.5 mm.

Figure 9:
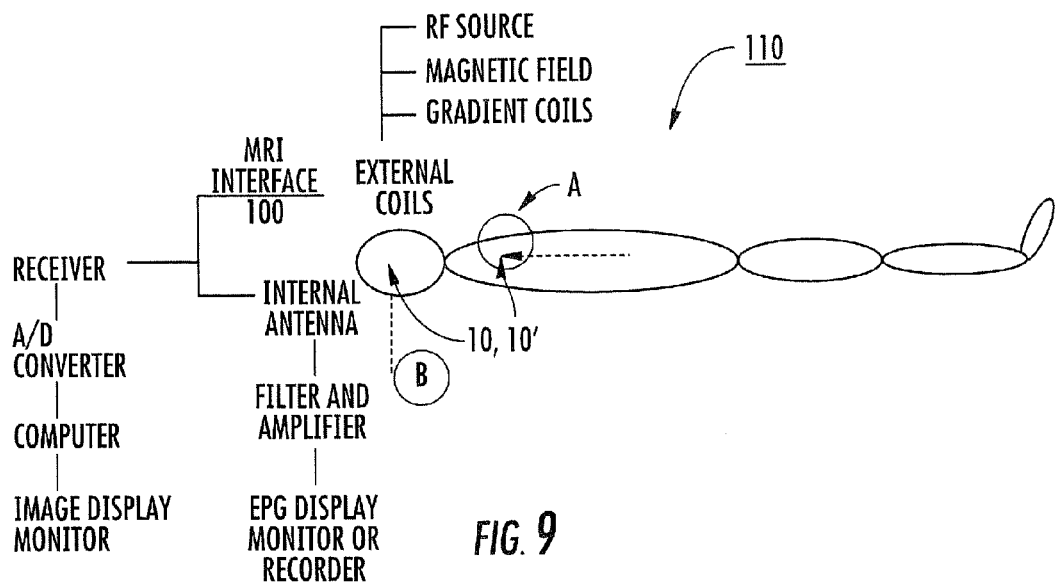
FIG. 9 is a schematic illustration of an MRI system according to embodiments of the present invention.
Figure 10:
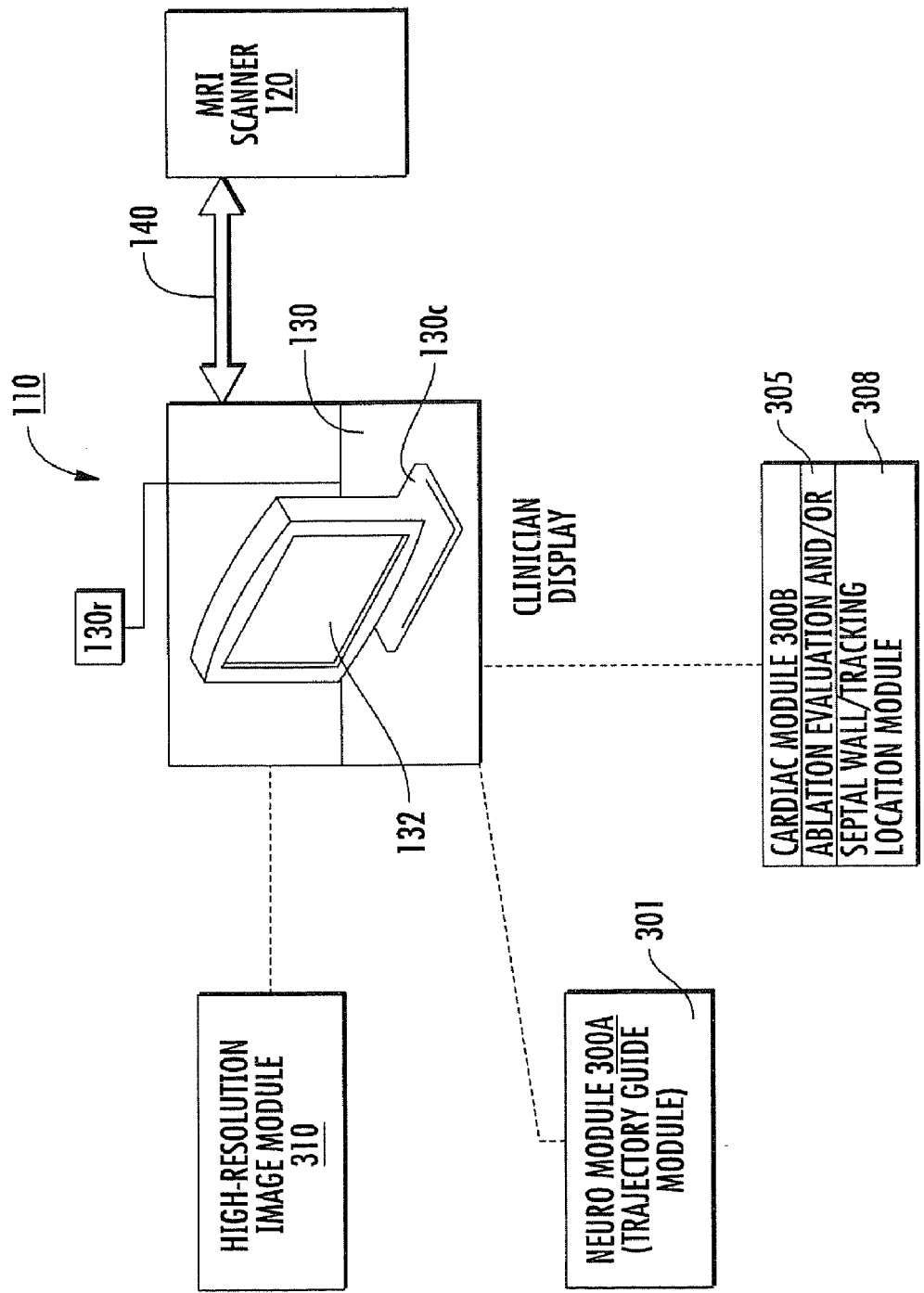
FIG. 10 is a schematic illustration of an MRI system according to embodiments of the present invention.

FIG. 9 illustrates that the probe 10, 10' can connect to an MRI scanner interface 100 and can include matching/tuning and decoupling circuit 124 and may optionally be incorporated into a system that communicates with a recorder 125 such as an EP recorder and/or monitor. The matching/tuning and decoupling circuit 124 can be provided as several circuits or integrated into one circuit that communicates with the MR Scanner and probe 10, 10'. Some or all of the components of the circuit 124 can be on the probe body, some or all in a connector associated therewith (not shown) and/or some or all may reside in a separate interface 100 in communication with the scanner 120 (FIG. 10).

In some embodiments, as discussed above, the probe 10, 10' can include at least one recording and/or ablating or stimulation electrode 30e, on a distal portion thereof. In this embodiment, the probe 10, 10' can define a multipurpose (e.g., bimodal) device that provides both high frequency (high frequency RF) and low frequency operational modes. For example, decoupling the antenna during microelectrode recording, ablation or stimulation and/or vice versa, decoupling the electrodes or other components used for recording, ablation or stimulation during RF transmission of the probe when the internal MRI antenna is operational in the receive mode (typically electrically isolated so that each mode is not concurrently operative). The low frequency mode may operate in the range of between about 100, Hertz (Hz) to less than about 15, MHz, typically between 100, Hz to about 1, kHz.

The high frequency mode typically operates at RF frequencies associated with the operational frequency of the MRI scanner (e.g., about 64, MHz for a 1.5T scanner).

Figure 8:
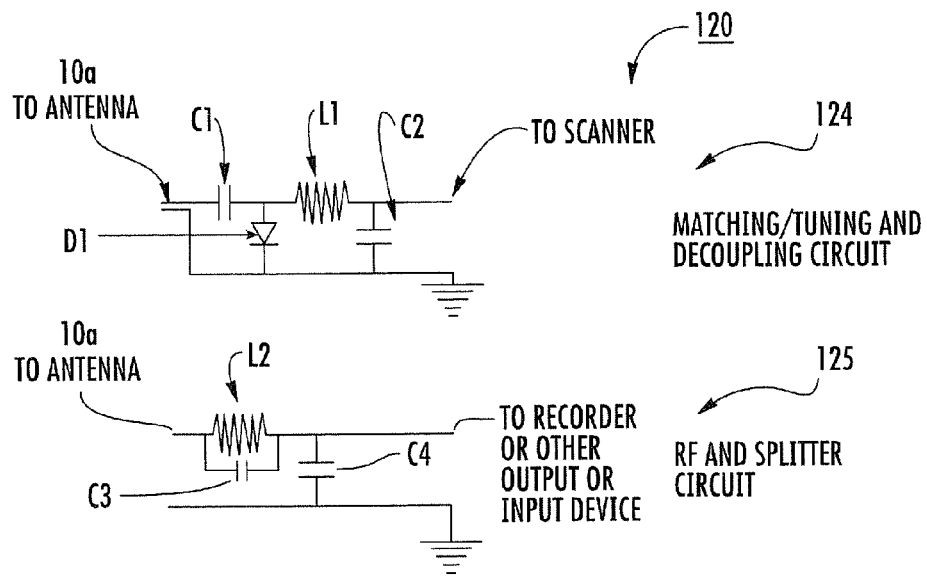
FIG. 8 is a schematic illustration of a matching tuning decoupling circuit and an RF-electrode splitter circuit that can be operatively associated with an MRI probe assembly according to embodiments of the present invention.

Generally stated, the assembly 10, 10' can be configured so that the MRI RF antenna 10a, can be matched and tuned at the MRI operating frequency of interest. The probe 10, 10' can include or be in communication with a matching/tuning and/or RF decoupling circuit 124 (FIG. 8) as well as a splitter circuit 125 (FIG. 8). The matching/tuning and RF decoupling circuit 124 is configured to decouple the probe during (high frequency) RF excitation so as to inhibit operation during active RF transmission (activating the antenna to receive MRI signals after RF excitation) associated with the MRI scanner. The splitter circuit 125 can be configured to allow two distinct modes of operation, one which electrically isolates the antenna 10a, (to allow low frequency operation, e.g., microelectric recording (electrophysiology and/or EKG) signal(s), ablation or stimulation of local tissue by the probe) and the other that allows high frequency operation of the antenna 10a. The splitter circuit 125 can include either a high pass and/or a low pass filter. Additional descriptions of suitable circuits are described in U.S. patent application Ser. No. 10/123,534, the contents of which are hereby incorporated by reference. Additional components of the antennas can include RF chokes as described for example, in U.S. Pat. No. 6,284,971, the contents of which are hereby incorporated by reference as if recited in full herein. For additional safety features that can be incorporated into the probe, see, co-pending U.S. patent application Ser. Nos. 12/090,583; 11/417,594;, and 12/047, 602, the contents of which are hereby incorporated by reference as if recited in full herein.

In some embodiments, the probe 10, 10' can have two or three primary operational modes with different electric transmission paths, which are electrically selectively engaged using the splitter circuit 125 (FIG. 8). In operation, during an MRI procedure, an RF excitation pulse is transmitted to a subject. The MRI antenna 10a, is decoupled during RF transmission, then operative during a receive cycle to receive signal from local tissue. The recording and/or ablation or stimulation electrode(s), where used, may also be electrically isolated via the splitter circuit 125 so that only the MRI antenna is active during MRI signal acquisition by the antenna 10a. The probe can have a proximal connector that connects to an MRI interface that communicates with the MRI scanner or that incorporates the MRI interface and directly connects to the MRI scanner.

During MRI guided clinical procedure, the probe 10, 10' can first be used as an MRI antenna to provide high resolution imaging of the target internal anatomy (such as neural or cardiac tissue) and/or to locate the position of the electrode (or probe) in the body by obtaining MRI signals and hence, images, that are acquired by the external coils and/or internal MRI antenna. As discussed above, one or more (where more than one electrode us used) of the electrodes 30e, can also be used to sense and output electrical signals from the target (e.g., neural) anatomy. In other embodiments, the electrodes can be used to deliver therapy such as stimulation or ablation treatments.

FIG. 9 illustrates conventional components of an MRI system 110 and the probe 10, 10'. In position "A", the probe 10, 10' is in the heart of a patient, such as for cardiac treatments according to particular embodiments of the present invention. In this embodiment, the system 110 may include filter and amplifier for monitoring ECG or electrophysiology signals in an MRI environment. In position "B", the probe 10, 10' is in the brain of the patient according to some embodiments of the present invention.

The imaging probe 10, 10' can be used in MRI systems for gene and/or stem-cell based therapy delivery or other neural therapy delivery and allow user-defined custom targets in the brain or to other locations (e.g., incorporated into or used with an injection catheter). In addition, embodiments of the systems can be used to ablate tissue in the brain, heart or other locations. In some embodiments, it is contemplated that the systems can be configured to treat AFIB in cardiac tissue, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine).

FIG. 10 illustrates an MRI guided interventional system 110 with an MRI scanner 120, a clinician workstation 130 with at least one circuit 130c, at least one display 132 and the imaging probe 10, 10'. An MRI scanner interface 140 may be used to allow communication between the workstation 130 and the scanner 120. The interface 140 and/or circuit 130c, may be hardware, software or a combination of same. The interface 140 and/or circuit 130c, may reside partially or totally in the scanner 120, partially or totally in the workstation 130, or partially or totally in a discrete device therebetween. The system 110 can be configured to render or generate real time (high-resolution) visualizations of the target anatomical space using MRI image data. The probe 10, 10' can include or cooperate with tracking, monitoring and/or interventional components for MRI-guided interventions or diagnosis.

As shown, the system can include a High-Resolution Image Module 310 that can use the MRI signal from the antenna 10a, to generate and/or display a high-resolution image. The system may also optionally or alternatively include a Neuro Module 300A and/or a Cardiac Module 300B. The Neuro Module 300A can communicate with or include a trajectory guide module 301 for tracking or visualizing a trajectory and/or local tissue. The Cardiac Module 300B can include an Ablation Evaluation Module 305 (for visualizing displaying lesions created during an MRI procedure) and/or a Septal Wall Tracking Location Module 308 for showing local anatomical tissue and location to facilitate clinical decisions on where to puncture the atrial wall during an intracardiac AFIB procedure, for example.

Figure 11:
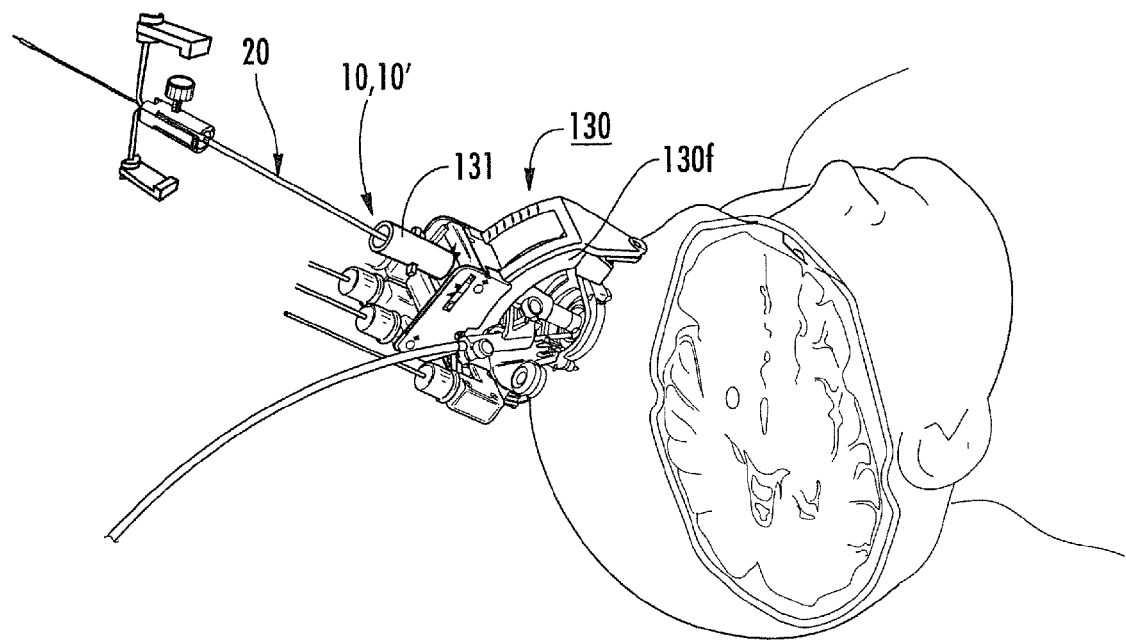
FIG. 11 is a schematic illustration of the imaging probe used with a targeting canula according to embodiments of the present invention.

FIG. 11 illustrates the probe 10, 10' can be used with a trajectory guide 130 having a targeting canula 131. The guide and targeting canula can provide X-Y adjustment and pitch and roll adjustment and may be controlled by a trajectory adjustment controller. The frame 130f, can include control arcs that cooperate with a platform to provide pitch and roll adjustments. The platform can allow for X-Y adjustments of the trajectory. For additional discussion of suitable trajectory guides, see, U.S. application Ser. No. 12/134,412, and co-pending, co-assigned U.S. patent application Ser. No. 12/236,950, the contents of which are hereby incorporated by reference as if recited in full herein.

Embodiments of the present invention may take the form of an embodiment combining software and hardware aspects, all generally referred to herein as a "circuit" or "module." In some embodiments, the circuits or modules include both software and hardware. Furthermore, certain modules or circuits of the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or other storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. Embodiments of the present invention, however, are not limited to any particular programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Computer program instructions may be provided to a processor of a general purpose computer, special purpose computer, ACIS or other programmable data processing apparatus to produce a machine, such that the instructions, which execute via the processor of the computer or other programmable data processing apparatus, create means for implementing the functions/acts specified in the blocks of the block diagrams/schematic illustrations.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The block diagrams of certain of the figures herein illustrate exemplary architecture, functionality, and operation of possible implementations of embodiments of the present invention. In this regard, each block represents a segment or portion of code, which comprises one or more executable instructions for implementing the specified logical function(s).

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures.

Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An elongate intrabody MRI-antenna probe having opposing distal and proximal portions, the distal portion having a single continuous length conductor arranged in a stack of two or three closely spaced substantially flat loops, wherein the stacked loops cooperate to define a flat-stacked loop MRI receive antenna, wherein the probe distal portion is planar and the flat stacked loop antenna has a flat shape on the distal portion of the probe, wherein the probe comprises at least one conductor that extends from the flat stacked loop antenna to an MR Scanner interface that connects to an MR Scanner, wherein the substantially flat loops have a long side and a short side, the long side having a length that is between about 20-50 mm, the short side having a width that is between about 1-5 mm, and wherein the flat-stacked loop MRI receive antenna is configured to generate a substantially homogenous signal profile and detect signal a forward looking distance beyond a distal end of the probe of at least about 1 mm.

2. The probe of claim 1, wherein the substantially flat loops have a substantially rectangular configuration with each loop being vertically aligned with the others such that a respective flat loop in the stack of flat loops resides substantially coextensive with neighboring flat loops, and wherein each flat substantially rectangular loop is defined by a conductor held by a layer of flexible substrate, such that the flexible substrate layers are stacked one over the other to define the vertically stacked flat loops.

3. The probe of claim 1, wherein at least two of the substantially flat loops define an electrically and physically closed loop, wherein the substantially flat loops are in communication with at least one capacitor, wherein the substantially flat loops have an inductance, and wherein the probe is tuned to an operating frequency of the MRI scanner using the inductance of the substantially flat loops and the at least one capacitor.

4. The probe of claim 1, wherein the probe comprises at least one recording electrode disposed on the distal portion, and wherein the probe has at least two operational modes, including a first MRI signal operational mode wherein the antenna member receives MRI signals from local tissue and a second operational recording signal mode wherein the recording electrode obtains electrical signals from local target tissue.

5. The probe of claim 1, wherein the probe comprises a high frequency operational mode associated with the MRI receive antenna and a low frequency operational mode associated with at least one electrode configured to ablate, stimulate or sense local electrical signals, and wherein the probe comprises a decoupler circuit that electrically isolates the at least one electrode from operation during the high frequency operational mode.

6. The probe of claim 1, further comprising: (a) an RF decoupling circuit in communication with the antenna configured to isolate the antenna during an MRI excitation RF transmission; and/or (b) a recording splitter circuit in communication with the antenna to decouple the antenna operational mode during a lower frequency mode associated with recording, ablation or stimulation.

7. The probe of claim 1, further comprising an RF decoupling circuit that includes or is in communication with a matching and tuning circuit that communicates with the MRI Scanner.

8. The probe of claim 1, further comprising a flexible catheter and/or sheath residing over the elongate probe.

9. The probe of claim 1, wherein the probe is sized and configured as a cardiac probe for MRI-guided AFIB (atrial fibrillation) treatment procedures.

10. The probe of claim 1, wherein the probe is sized and configured as a deep brain probe used for MRI-guided interventional or diagnostic procedures.

11. The probe of claim 1, wherein the antenna is able to detect local MRI signal and generate a signal with at least about a 6 mm diameter signal penetration spot in an image.

12. An MRI cardiac system, comprising:
a planar intracardiac probe comprising at least one conductor configured in a stack of abutting layers of substantially flat loops on a distal portion of the probe, wherein the stacked flat loops have a long side and a short side, the respective long sides having a length that is between about 5 to 30 mm or 20-50 mm, and wherein the stacked flat loops cooperate to define an MRI receive antenna, wherein the probe comprises at least one conductor that extends from the stacked loops to an MR Scanner interface that connects to an MR Scanner, and wherein the probe comprises or is in communication with matching and decoupling circuitry in communication with the receive antenna and the MRI Scanner.

13. The system of claim 12, further comprising a clinician workstation with a display in communication with the probe configured to display high-resolution MRI images using image data from the probe receive antenna.

14. The system of claim 12, wherein the probe is sized and configured to enter a port in an atrial wall of a respective patient during an atrial fibrillation treatment procedure.

15. An MRI neurological system, comprising:
a planar intrabrain probe comprising at least one conductor configured in a stack of abutting layers of substantially flat loops on a distal portion of the probe, wherein the stacked flat loops have a long side and a short side, the respective long sides having a length that is between about 5-30 mm or 20-50 mm, and wherein the stacked flat loops cooperate to define an MRI receive antenna, wherein the probe comprises at least one conductor that extends from the stacked loops to an external MRI Scanner interface that connects to an MRI Scanner, and wherein the probe comprises or is in communication with matching and decoupling circuitry in communication with the receive antenna and the MRI scanner.

16. The system of claim 15, further comprising a clinician workstation with a display in communication with the probe configured to display high-resolution MRI images using image data from the probe receive antenna.

17. The system of claim 15, further comprising a targeting canula held by a trajectory guide adapted to be positioned on a skull of a patient, and wherein the probe is configured to be held by the targeting canula during a deep brain procedure.

18. The system of claim 15, wherein the flat loops each with a short side that defines a width dimension and a long side that defines a length dimension, and wherein the long side is about 35 mm and the short side is about 1.5 mm thereby providing a length dimension that is at least 10 times greater than the width dimension.

19. An elongate intrabody MRI-antenna probe having opposing distal and proximal portions, the distal portion having a single continuous length conductor arranged in a stack of two or three closely spaced substantially flat loops, wherein the stacked loops cooperate to define a flat-stacked loop MRI receive antenna, wherein the probe distal portion is planar and the flat stacked loop antenna has a flat shape on the distal portion of the probe, wherein the probe comprises at least one conductor that extends from the flat stacked loop antenna to an MR Scanner interface that connects to an MR Scanner, wherein the substantially flat loops have a long side and a short side, the long side having a length that is between about 5-30 mm, and wherein the flat-stacked loop MRI receive antenna is configured to generate a substantially homogenous signal profile and detect signal a forward looking distance beyond a distal end of the probe of at least about 1 mm.

20. The probe of claim 19, wherein the antenna is able to detect local MRI signal and generate a signal with at least about a 6 mm diameter signal penetration spot in an image.

* * * * *